United States Patent [19]

Montag et al.

[11] Patent Number: 4,801,571

[45] Date of Patent: Jan. 31, 1989

[54] CATALYST AND PROCESS FOR PRODUCTION OF AN ALPHA, BETA-ETHYLENICALLY UNSATURATED MONOCARBOXYLIC ACID

[75] Inventors: Ruth A. Montag, Naperville; Stephen T. McKenna, Lisle, both of Ill.

[73] Assignee: Amoco Corporation, Chicago, Ill.

[21] Appl. No.: 71,476

[22] Filed: Jul. 9, 1987

Related U.S. Application Data

[63] Continuation-in-part of Ser. No. 891,755, Jul. 31, 1986, abandoned.

[51] Int. Cl.$^4$ .............................................. B01J 23/14
[52] U.S. Cl. ................... 502/236; 502/242; 502/243; 562/599
[58] Field of Search ................ 502/236, 242, 243

[56] References Cited

U.S. PATENT DOCUMENTS

| | | | |
|---|---|---|---|
| 1,879,022 | 9/1932 | Barclay | 502/236 |
| 3,520,915 | 7/1970 | Kominami et al. | 502/242 X |
| 3,840,587 | 10/1974 | Pearson | 502/243 X |
| 3,840,588 | 10/1974 | Pearson | 502/243 X |
| 3,933,888 | 1/1976 | Schlaefer | 502/164 X |
| 4,147,718 | 4/1979 | Gaenzler et al. | 502/211 X |
| 4,567,030 | 1/1986 | Yuasa et al. | 502/236 X |

*Primary Examiner*—Patrick P. Garvin
*Attorney, Agent, or Firm*—Reed F. Riley; William H. Magidson; Ralph C. Medhurst

[57] ABSTRACT

A catalyst and process for production of an alpha, beta-ethylenically unsaturated monocarboxylic acid made by condensing formaldehyde with, for example, propionic acid, which catalyst is made from a $SiO_2$-$SnO_2$ mixed-oxide component consisting of porous silica gel and tin (IV) oxide and a cesium ion component.

38 Claims, 2 Drawing Sheets

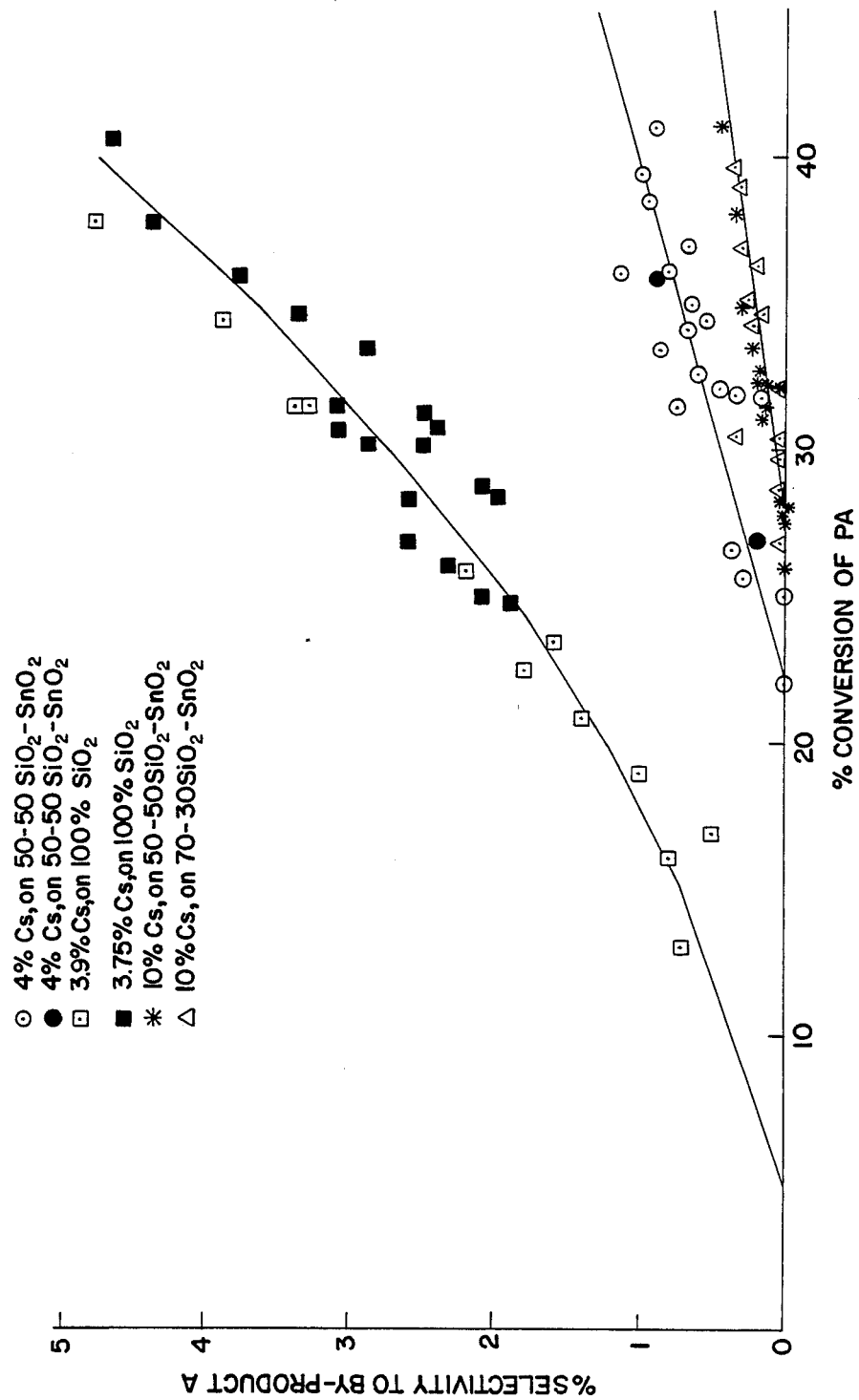

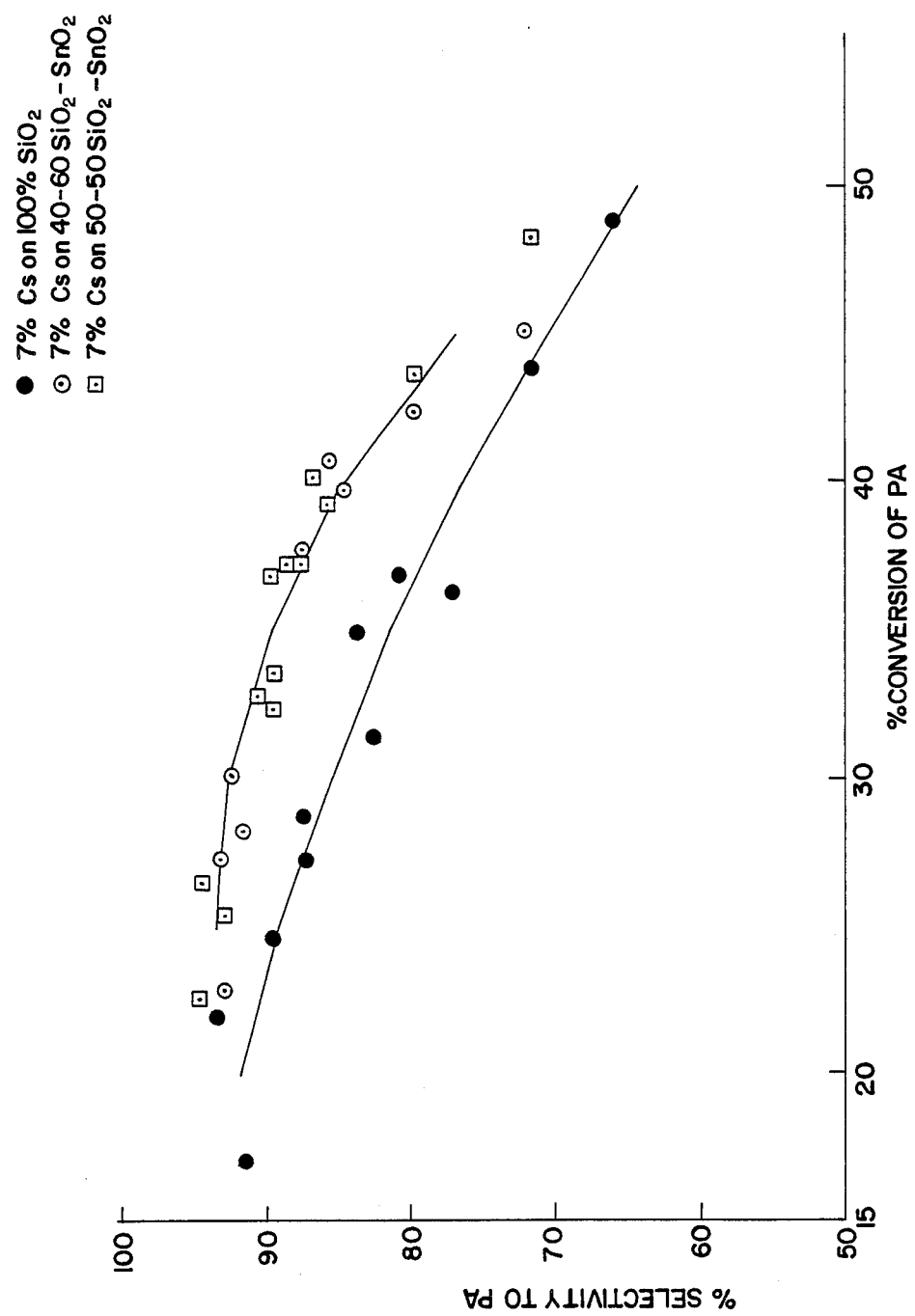

CATALYST AND PROCESS FOR PRODUCTION OF AN ALPHA, BETA-ETHYLENICALLY UNSATURATED MONOCARBOXYLIC ACID

CROSS REFERENCE TO RELATED APPLICATIONS

This application is a continuation-in-part of U.S. Ser. No. 891,755, filed July 31, 1986 and now abandoned.

FIELD OF THE INVENTION

This invention relates to a catalyst and process for the production of an alpha, beta-ethylenically unsaturated monocarboxylic acid. More specifically, this invention relates to a catalyst and process for synthesizing methacrylic acid by the vapor-phase condensation of propionic acid with formaldehyde.

BACKGROUND OF THE INVENTION

Unsaturated carboxylic acids such as methacrylic acid, and the esters of such acids such as methyl methacrylate, are widely used for the production of corresponding polymers, resins and the like. Typically, a saturated monocarboxylic acid, such as propionic acid (PA), can be catalytically reacted with formaldehyde (FA) to produce an alpha, beta-ethylenically unsaturated monocarboxylic acid, such as methacrylic acid (MA), and water as a co-product. The produced alpha, beta-ethylenically unsaturated monocarboxylic acid can be esterified to a polymerizable, alpha, beta-ethylenically unsaturated monocarboxylic acid ester, such as methyl methacrylate (MMA).

MMA is a monomer containing a carbon-carbon double bond ($>C=C<$) and a carbonyl group

Polymers derived from MMA are sometimes also referred to as "acrylic" or "acrylic-type" polymers. The MMA-type polymers have desirable transparency, weatherability and physical strength properties. Typical end-uses for MMA-derived polymers include acrylic sheet that can be fabricated into signs, advertising displays, lighting fixtures, glazing materials, structural panels and the like, molding resins for automobile, bus, truck and other vehicular tail-light lenses, plumbing and electrical fixtures and the like, as well as constituents of a variety of surface coatings, adhesives, inks, floor polishes and the like.

Generally, the condensation reaction to synthesize an alpha, beta-ethylenically unsaturated aliphatic monocarboxylic acid, such as MA, takes place in the vapor or gaseous phase and in the presence of a catalyst which can be basic, acidic, or substantially neutral. In the absence of the catalyst, reactants typically require addition of heat energy to overcome an "energy of activation" of the reaction, which can be a barrier to formation of the desired products. Also, in the instance where the reactants are chemically converted to a variety of products, a catalyst may tend to increase the rate of formation of one product relative to one or more of the other products. Such a catalyst is said to possess increased selectivity qualities, often a consideration when choosing a catalyst for commercial production purposes.

Reaction temperature plays an important role in the activity of a catalyst, another important consideration. At a particular temperature, for example, a commercially-acceptable percentage of the reactants might be converted to a desired product, with only a relatively minor percentage of the reactants being converted to undesired by-products. Typically, an increase in the temperature of the reaction not only tends to increase the rate at which the reactants are converted to the desired product or products, but also tends to increase the rate at which undesired by-products are produced as well.

Catalysts commonly used for reacting PA with FA to produce MA are alkali metals supported on silica. Typical catalysts of this type are disclosed in U.S. Pat. No. 4,147,718 to Gaenzler et al., U.S. Pat. No. 3,933,888 to Schlaefer, U.S. Pat. No. 3,840,587 to Pearson, U.S. Pat. No. 3,247,248 (see also Canadian Pat. No. 721,773) to Sims et al., and U.S. Pat. No. 3,014,958 to Koch et al.

These prior-art catalysts, while effecting condensation of PA with FA to produce MA, unfortunately also generate undesirable by-products that have to be separated from the produced MA. Relatively low conversion and/or selectivity performance values, together with relatively low catalyst useful-life values, are additional drawbacks.

Generally, when PA and FA are reacted in the vapor phase, and in the presence of a catalyst, to produce desired product MA and co-product $H_2O$, a variety of undesirable by-products are simultaneously produced as well. The more common of these undesirables are hereinafter referred to as by-product A (2,5-dimethyl-2-cylopenten-1-one), by-product B (2,4,4-trimethyl-gamma-butyrolactone), and by-product 3-P (3-pentanone). The presence of these by-products is generally undesirable because current MA-esterification and MMA-polymerization technology requires separation of these by-products either from the MA before it is esterified to MMA, or before the produced MMA is polymerized. It is additionally desirable to remove by-product A from the MA prior to esterification as the presence of this by-product tends to interfere with the desired formation of MMA. In particular, the presence of by-product A in the MA tends to cause an undesirable polymerization of MA and attendant separation problems. Loss of product also may become significant.

Accordingly, it would be desirable to have a catalyst which provides improved PA conversion, which decreases undesirable by-product generation, and which enhances useful catalyst life. The catalyst, and the catalyst support, of the present invention meet the foregoing desires.

Not only has the catalyst of the present invention been observed to be more active than conventional catalysts (i.e. the present catalyst has been observed to enable the MA-synthesizing, gas-phase, condensation reaction of PA with FA to take place at a relatively lower temperature for a given conversion); but the catalyst has also been observed to exhibit increased selectivity toward production of MA as well. While reduction of reaction temperature tends to increase the useful life of the catalyst per se, a reduced operating temperature may reduce overall operating costs as an added benefit. The reduction in the amounts of the undesirable by-products, moreover, tends to reduce, and may even eliminate, the costs attendant to (1) the removal of the undesirable by-products from the MA prior to esterification, and (2) the purification of the MMA prior to polymerization.

SUMMARY OF THE INVENTION

The particulate catalyst of the present invention is suitable for synthesis of an unsaturated carboxylic acid. This catalyst is especially suitable for condensation of a saturated monocarboxylic acid, such as propionic acid, with formaldehyde to produce an alpha, beta-ethylenically unsaturated monocarboxylic acid, such as methacrylic acid.

The present catalyst comprises $SiO_2$, $SnO_2$ (together referred to below as "$SiO_2$-$SnO_2$ mixed-oxide") and cesium ions. The cesium ions, the primary catalytically active ingredient of the present catalyst, are present on the catalyst in the $+1$ oxidation state and in an amount of about 1 to about 15 percent by weight, preferably in an amount of about 4 to about 10 percent by weight, and more preferably in an amount of about 7 to about 10 percent by weight, based on the weight of the catalyst. The present catalyst may also include a relatively small amount of boron.

The present $SiO_2$-$SnO_2$ mixed-oxide comprises a porous silica gel, and particulate $SnO_2$ having a particle size of no more than about 10,000 microns. This $SiO_2$-$SnO_2$ mixed-oxide contains $SiO_2$ in an amount of about 5 to about 85 percent by weight of the total, and $SnO_2$ in an amount of about 95 to about 15 percent by weight of the total. The present $SiO_2$-$SnO_2$ mixed-oxide has a surface area of about 10 to about 300 $m^2$/gram, preferably about 50 to about 135 $m^2$/gram, a porosity of less than about 5 $cm^3$/gram, preferably less than about 1 $cm^3$/gram, and a pore size distribution such that less than about 10 percent of the pores present in the catalyst have a pore diameter greater than about 750 Angstroms.

Preferably, the relative amounts of $SiO_2$ and $SnO_2$, based on the weight of the $SiO_2$-$SnO_2$ mixed-oxide, are about 30 to about 70 percent by weight $SiO_2$ and about 70 to about 30 percent by weight $SnO_2$, more preferably about 40 to about 60 percent by weight $SiO_2$ and about 60 to about 40 percent by weight $SnO_2$. Particularly preferred are mixtures of tin and silicon oxides containing about 40 to about 50 percent by weight $SiO_2$ and about 60 to about 50 percent by weight $SnO_2$. Most preferred is a mixture of oxides containing about 50 percent by weight of each of $SiO_2$ and $SnO_2$.

Of the pores present in the $SiO_2$-$SnO_2$ mixed-oxide, a major portion preferably has a pore diameter of about 50 to about 500 Angstroms, and more preferably has a pore diameter of about 80 to about 300 Angstroms.

Average cesium ion site density on the $SiO_2$-$SnO_2$ mixed-oxide surface is preferably about 1 to about 10 cesium ions, in the $+1$ oxidation state, per square nanometer of the catalyst support surface area. More preferably, the average cesium ion site density on the catalyst support surface is about 2 to about 7 cesium ions per square nanometer of the $SiO_2$-$SnO_2$ mixed-oxide surface area.

A cesium compound can be placed on either oxide of the $SiO_2$-$SnO_2$ mixed-oxide, or both, before they are admixed or afterwards. It is likely that the cesium compound on the surface of the $SnO_2$ component, if present initially, migrates to the $SiO_2$ component of the $SiO_2$-$SnO_2$ mixed-oxide under reaction conditions.

Another aspect of the present invention is directed to methods for making the present catalyst and $SiO_2$-$SnO_2$ mixed-oxide. One way of making the present catalyst is to produce a freely-flowing slurry having a $SiO_2$/$SnO_2$ weight ratio of about 0.05 to about 6 and a $Cs/(SiO_2+SnO_2+Cs)$ weight ratio of about 0.01 to about 0.15, solidify the produced slurry to a gel, dry the obtained gel to a crushable solid state, and calcine the dried gel for a time period sufficient to remove most of the adsorbed moisture therefrom. The freely-flowing slurry is produced by combining, with agitation, desired amounts of a silica sol containing silica particles of about 50 to about 200 Angstroms in diameter, a slurry containing $SnO_2$ particles, and a cesium compound able to provide cesium in the $+1$ oxidation state on the catalyst surface.

Preferably, the silica sol is aqueous and has a silica content of about 14 to about 34 weight percent.

The cesium compound is preferably a salt selected from the group consisting of cesium carbonate, cesium hydroxide, cesium phosphate, cesium fluoride and cesium nitrate, and more preferably is cesium carbonate.

The produced, freely-flowing slurry can include boric acid as a source of boron, and/or ammonium nitrate as a gelling promoter. The pH of the produced, freely-flowing slurry can be adjusted to a value of about 7, prior to solidification, to reduce the time period required to effect gelling. An inorganic acid, preferably nitric acid, is used for pH-adjustment purposes.

The produced gel can be formed into beads, cylinders or other suitable shapes of a desired configuration, and then dried. Alternatively, the produced gel can be dried first and then subjected to a size-reduction operation. The drying can be carried out either at about atmospheric pressure, or at a subatmospheric pressure and at a relatively lower temperature. Preferably, the gel is dried to substantially constant weight.

Calcining of the dried gel preferably is carried out for a time period sufficient to reduce the weight of the dried gel by at least about 2 weight percent. Preferably, calcination is carried out to a weight loss of about 3 to about 4 wt. %.

The catalyst of the present invention can also be made by first preparing the above-described mixture of silicon and tin (IV) oxides and then contacting (such as by impregnation) the mixture with the cesium compound.

Still another method of making the catalyst of the instant invention is to physically mix the porous silica gel impregnated with a cesium compound with the tin (IV) oxide. This mixture can then be made into a form suitable for use in the reactor chosen.

Yet another way of making the catalyst is to grind the porous silica gel containing the cesium compound with the tin (IV) oxide and to form the result into a catalyst suitable for commercial use.

BRIEF DESCRIPTION OF THE DRAWINGS

In the drawings,

FIG. 1 is a graph showing percent selectivity toward production of by-product A as a function of percent conversion of propionic acid (PA) to methacrylic acid (MA); and FIG. 2 is a graph comparing the conversion and selectivity performance of the cesium-containing $SiO_2$-$SnO_2$ mixed-oxide catalyst of the present invention to that of a cesium-containing control catalyst having silica as the catalyst support.

DETAILED DESCRIPTION OF PREFERRED EMBODIMENTS

The catalyst of the present invention is particularly well-suited for the gas-phase synthesis of methacrylic acid (MA) via condensation of formaldehyde (FA) with propionic acid (PA). The catalyst of the present invention, a three-component catalyst containing porous silica gel, tin (IV) oxide and supported cesium ions, catalytically induces this condensation reaction. The cesium ions are present on the catalyst surface in the +1 oxidation state and in amounts discussed hereinbelow.

The vapor-phase condensation reaction takes place in a reactor suitable for effecting desired heterogeneous catalysis. The reactor effluent commonly includes not only the desired synthesis product, MA, and water as a co-product of the desired condensation reaction, but also unreacted PA and FA, a variety of organic by-products and certain relatively volatile gases as well. The thus-synthesized MA can be separated from the unconverted PA and FA reactants and the above-identified co-product and by-products, then esterified with a suitable $C_1$ to $C_4$ aliphatic alcohol such as methanol (MeOH), and thereafter can be purified to obtain a polymer-grade ester such as methyl methacrylate (MMA).

In the ensuing detailed description, certain terms will be utilized for purposes of conciseness, and for purposes of elucidating the features and advantages of the present invention. These terms are defined hereinbelow.

The term "activity of a catalyst" as used herein means the relative ease or difficulty of the catalyst at a given temperature to effect chemical conversion of the reactants to the desired product or products.

The terms "average pore radius" and "average pore diameter" as used herein mean the respective dimensions as determined utilizing the well-known BET nitrogen desorption method. [See, e.g., S. Brunauer et al., J.A.C.S., 60, 309, (1938).] The reported values are those representing a pore radius or diameter where one-half of the pore volume present exhibits a radius or diameter smaller than the reported value and one-half of the pore volume present exhibits a radius or diameter greater than the reported value, respectively.

The term "catalyst" as used herein broadly means a substance which increases the rate at which a thermodynamically-allowable chemical reaction takes place. Typically, relatively small percentages of catalyst markedly affect the rate of a given chemical reaction.

The term "calcining" as used herein means subjecting dried material to a temperature of at least about 250° C. (about 480° F.).

The term "colloid" as used herein means a suspension of finely divided particles that do not settle out of, and cannot be readily filtered from, the medium in which they are suspended.

The term "colloidal silica" as used herein describes a dispersion of typically millimicron-size $SiO_2$ particles in an aqueous or organic solvent. Colloidal silica is also sometimes referred to as "silica sol." Illustrative silica sols are those commercially available from the Nalco Chemical Company, Oakbrook, Ill. 60521, under the designations Nalco 1034-A and Nalco 2326 silica sols.

Nalco 1034-A silica sol has a silica concentration of about 34 weight percent, based on the weight of the silica sol, a mean silica particle size of about 20 nanometers, a pH of about 3.2, a particulate surface area of about 150 m$^2$/gram of $SiO_2$, a viscosity of about 10 centipoises, and a $Na_2O$ content of less than about 0.05 wt. %, based on the weight of the silica sol.

Nalco 2326 silica sol is an ammonium-stabilized silica sol, has a silica concentration of about 14.5 weight percent, based on the weight of the silica sol, has a mean silica particle size of about 5 nanometers, exhibits a pH of about 9, has a particulate surface area of about 600 m$^2$/gram of $SiO_2$, has a viscosity of about 5 centipoises, and has a $Na_2O$ content of less than about 0.05 wt. %, based on the weight of the silica sol.

The term "drying" as used herein means subjecting the material to be dried to a temperature of no more than about 250° C. (about 480° F.).

The term "silica gel" as used herein describes a coherent, rigid, continuous three-dimensional network of spherical particles of colloidal silica. Silica gel has not been observed to possess an ordered crystal structure, but rather, has been observed to be constituted primarily by silica ($SiO_2$) in amorphous state. Silica gel per se is known to catalyze certain chemical reactions, and is used as a catalyst carrier or support in a number of commercial catalytic processes.

The term "WHSV" as used herein means weight hourly space velocity, and is expressed as grams of feed per gram of catalyst per hour.

Additional definitions include the following equations.

Yield ($Y$), based on propionic acid:
$$\% Y (PA) = \frac{\text{mols of MA produced}}{\text{mols of PA in feed}} \times 100$$

Yield ($Y$), based on formaldehyde:
$$\% Y (FA) = \frac{\text{mols of MA produced}}{\text{mols of FA in feed}} \times 100$$

Methacrylic acid selectivity ($S$), based on propionic acid:
$$\% S (PA) = \frac{\text{mols of MA produced}}{\text{mols of PA reacted}} \times 100$$

Methacrylic acid selectivity ($S$), based on formaldehyde:
$$\% S (FA) = \frac{\text{mols of MA produced}}{\text{mols of FA reacted}} \times 100$$

Conversion ($C$):
$$\% C = \frac{\% Y}{\% S} \times 100$$

Similar terminology will be utilized to describe the yield, selectivity and conversion of the organic by-products when the performance of the present catalyst is discussed.

The catalyst suitable for the purposes of the present invention is constituted principally by porous silica gel particles and tin (IV) oxide particles and has the catalytically active ingredient, cesium ion, on the surface thereof. Neither porous silica gel nor tin (IV) oxide exerts a noticeable catalytic effect vis-a-vis the condensation reaction; however, the combination of these constituents provides certain advantages with respect to the overall performance of the present catalyst under process conditions as will be discussed in greater detail hereinbelow.

The relative amounts of $SiO_2$ and $SnO_2$ in the present $SiO_2$-$SnO_2$ mixed-oxide can vary over a relatively wide range. In particular, it can contain about 5 to about 85 weight percent $SiO_2$ and about 95 to about 15 weight percent $SnO_2$. The catalyst of the present invention comprises the foregoing $SiO_2$-$SnO_2$ mixed-oxide and cesium ions.

The cesium ions, the catalytically active ingredient of the present invention, are present on the present catalyst support surface in the +1 oxidation state and in an amount of about 1 to about 15 percent by weight, based on the weight of the catalyst. Preferably, the cesium ions are present in an amount of about 4 to about 10 percent by weight, and more preferably in an amount of about 7 to about 10 percent by weight, based on the weight of the catalyst. The average cesium ion site density on the catalyst surface is preferably about 1 to about 10 cesium ions per square nanometer of the catalyst surface area, and more preferably is about 2 to about 7 cesium ions per square nanometer of the catalyst surface area. The average cesium ion site density in any given instance is determined by the relative amount of cesium compound used in making the present catalyst, together with the surface area of the present catalyst.

The $SiO_2$-$SnO_2$ mixed-oxide of the present invention comprises a porous silica gel, and $SnO_2$ particles having a particle size of up to about 1 centimeter (10,000 microns) distributed substantially uniformly throughout the silica gel. Preferably, the $SnO_2$ particles are less than about 100 microns (0.1 mm) in diameter; more preferably, the $SnO_2$ particles are less than about 10 microns (0.01 mm) in diameter. They should not be smaller than about 0.03 microns (about 300 Angstroms) in diameter. In preparing the $SiO_2$-$SnO_2$ mixed-oxide, any suitable $SnO_2$-containing media can be utilized. However, use of $SnO_2$ colloids is not preferred.

The catalyst has a surface area of about 10 to about 300 $m^2$/gram, preferably about 50 to about 135 $m^2$/gram, a porosity of less than about 5 $cm^3$/gram, preferably less than about 1 $cm^3$/gram, and a pore size distribution such that less than about 10 percent of the pores present in the catalyst have a pore diameter less than about 50 Angstroms, and such that less than about 10 percent of the pores present in the catalyst have a pore diameter greater than about 750 Angstroms.

The pore size distribution can be controlled by appropriate selection of the silica particle size and particle size distribution in the silica sol that is used as one of the starting materials for the present catalyst support. For example, a silica particle size of about 20 nanometers (about 200 Angstroms) will provide a relatively larger pore size than a silica particle size of about 5 nanometers (about 50 Angstroms).

The relative amounts of $SiO_2$ and $SnO_2$ present, based on the weight of the $SiO_2$-$SnO_2$ mixed-oxide of the present invention, are preferably about 30 to about 70 percent by weight $SiO_2$ and about 70 to about 30 percent by weight $SnO_2$, and more preferably about 40 to about 60 percent by weight $SiO_2$ and about 60 to about 40 percent by weight $SnO_2$. Particularly preferred is a $SiO_2$-$SnO_2$ mixed-oxide containing about 40 to about 50 percent by weight $SiO_2$ and about 60 to about 50 percent by weight $SnO_2$. Most preferred is a material containing about 50 percent by weight of each of $SiO_2$ and $SnO_2$.

Of the pores present in the catalyst, a major portion preferably has a pore diameter of about 50 to about 500 Angstroms, and more preferably has a pore diameter of about 80 to about 300 Angstroms. Most preferably, the average pore diameter is about 90 to about 200 Angstroms.

The $SiO_2$-$SnO_2$ mixed-oxide-and-Cs-containing catalysts of the present invention can be prepared in a preferred manner by forming a freely-flowing slurry containing silica sol, $SnO_2$, and a cesium compound able to provide cesium (Cs) in the +1 oxidation state. The slurry is then gelled, dried, and calcined.

A preferred method for making the catalyst of the present invention comprises the steps of producing a freely-flowing slurry having a $SiO_2$/$SnO_2$ weight ratio of about 0.05 to about 6 and a $Cs/(SiO_2+SnO_2+Cs)$ weight ratio of about 0.01 to about 0.15, solidifying the produced slurry to a gel, drying the obtained gel to a crushable solid state, and calcining the dried gel for a time period sufficient to remove primarily adsorbed moisture therefrom. This freely-flowing slurry is produced by combining the respective amounts of (1) a silica sol containing silica particles of about 50 to about 200 Angstroms in diameter, (2) a slurry containing $SnO_2$ particles less than about 10 microns in diameter, and (3) a cesium compound able to provide cesium ions in the +1 oxidation state on the catalyst support surface. The foregoing slurry constituents are combined with agitation to produce a substantially uniform admixture.

Preferably, the silica sol that is used in the production of the freely-flowing slurry is aqueous and has a silica content of about 14 to about 34 weight percent, based on the weight of the silica sol; and the contained silica has a mean particle size of about 5 to about 20 nanometers (about 50 to about 200 Angstroms). As pointed out above, however, the pore size of the produced catalyst can be adjusted by modulating the particle size distribution of the silica sol utilized. For example, silica sols having different mean particle sizes can be commingled in various proportions prior to gelling.

The cesium compound, for purposes of the present invention, can be relatively volatile, water or solvent soluble, or thermally decomposable.

Illustrative of the thermally decomposable cesium compounds that can be utilized are cesium borofluoride ($CsBF_4$), cesium bromate ($CsBrO_3$), cesium bromochloride iodide (CsIBrCl), cesium dibromoiodide ($CsIBr_2$), cesium perchlorate ($CsClO_4$), cesium chloroiodide ($CsICl_2$), cesium dichloroiodide ($CsICl_2$), cesium hydride (CsH), cesium permanganate ($CsMnO_4$), cesium nitrate ($CsNO_3$), cesium oxide ($Cs_2O$), and the like.

Illustrative of the relatively volatile cesium compounds that can be utilized are cesium dibromochloride ($CsBr_2Cl$), cesium formate [$Cs(CHO_2 \cdot H_2O)$], cesium hydrofluoride (CsF·HF), cesium hydrogencarbide ($CsHC_2$), cesium hydroxide (CsOH), cesium pentaiodide ($CsI_5$), cesium triiodide ($CsI_3$), cesium hydrogen nitrate ($CsNO_3 \cdot NHO_3$), cesium dihydrogen nitrate ($CsNO_3 \cdot 2HNO_3$), cesium peroxide ($Cs_2O_2$), cesium trioxide ($Cs_2O_3$), cesium propionate [$Cs(C_3H_5O_2)$], and the like.

Illustrative of the water-soluble cesium compounds that can be utilized are cesium acetate [$Cs(C_2H_3O_2)$], cesium azide ($CsN_3$), cesium benzoate [$Cs(C_7H_5O_2)$], cesium monobromide (CsBr), cesium carbonate ($Cs_2CO_3$), cesium hydrogen carbonate ($CsHCO_3$), cesium chlorate ($CsClO_3$), cesium chloride (CsCl), cesium chromate ($Cs_2CrO_4$), cesium fluoride (CsF), cesium fluosilicate ($Cs_2SiF_6$), cesium formate [$Cs(CHO_2)$], cesium hydroxide (CsOH), cesium iodide (CsI), cesium nitrate ($CsNO_3$), cesium oxalate [$Cs_2(C_2O_4)$], cesium salicylate [$Cs(C_7H_5O_3)$], cesium selenate ($Cs_2SeO_4$), cesium hydrogen tartrate [$CsH(C_4H_4O_6)$], and the like. The cesium compound can also be soluble in a water-miscible or water-immiscible organic solvent.

Specifically, the cesium compound is preferably selected from the group consisting of cesium carbonate, cesium hydroxide, cesium phosphate, cesium propionate, cesium fluoride and cesium nitrate, and more preferably is cesium carbonate or cesium propionate.

More particularly, the cesium is preferably contained in an aqueous solution of relatively high cesium concentration, usually approaching saturation for the particular compound that is utilized. More dilute solutions can be used, if desired.

The produced, freely-flowing slurry can include boric acid as a boron source and/or ammonium nitrate as a gelling promoter. To promote gelling rate, the pH of the produced, freely-flowing slurry can be adjusted to about 7. An inorganic acid, preferably nitric acid, is used for such a desired pH-adjustment purpose.

Many of the cesium salts disclosed herein, as well as $SnO_2$, per se, can act as gelling promoters, at least to a limited extent. It is preferable, however, to add a specific gelling promoter, so as to provide the present catalyst support, or the present catalyst per se, with the desired herein-described physical properties within a given time period. A suitable gelling promoter for this purpose is ammonium nitrate ($NH_4NO_3$). The concentration of the gelling promoter in the slurry can be in the range of about 0.5 to about 1.5 wt. %, based on the weight of the slurry.

In one method aspect of this invention, the produced gel can be formed into beads, cylinders or other suitable shapes of a desired configuration, and then dried. For example, the gel can be dried as a sheet-form material.

Preferably, the drying is carried out at about atmospheric pressure. Alternatively, the drying step can be carried out at a subatmospheric pressure and at a relatively lower temperature, e.g. about 150° C. (about 300° F.) or below. The gel is then dried to a crushable solid state. It is preferred to dry the gel to substantially constant weight. Drying can be carried out in ambient atmosphere or in an inert atmosphere, as desired.

When it is desirable to dry the gel as a sheet-form material, the dried gel can be comminuted, such as by crushing, prior to further heat treatment.

Calcining of the dried gel is carried out for a time period sufficient to reduce the weight of the dried gel by at least about 2 weight percent. Preferably, calcination is carried out to a weight loss of about 3 to about 4 wt. %. Calcining preferably is carried out at a temperature in the range from about 450° C. to about 600° C. for a time period of up to about 8 hours. Calcination temperature and time are catalyst preparation parameters which can be used to fine tune catalyst selectivity and activity. For a given cesium loading as calcination temperature increases initial surface area decreases. This changes the density of cesium ions on the surface influencing catalyst selectivity. Longer calcination times can also result in lower initial surface area for the catalyst.

In the examples appearing below, the following conditions were maintained, and the following equipment and procedures were used, unless otherwise indicated.

Reagent-grade trioxane was used as the FA source; however, in the conversion of PA with FA in the presence of the catalyst of this invention to synthesize MA any suitable source of formaldehyde can be used such as formalin, paraformaldehyde, methanolic formaldehyde, substantially anhydrous formaldehyde, and the like.

A laboratory minireactor was used to determine the MA-synthesis performance of each catalyst. All experimental determinations or runs were conducted at a PA/FA mole ratio of about 3/2. The minireactor comprised an elongated 12.7 mm. (millimeter) O.D. quartz tube having an externally-controllable thermowell longitudinally disposed in, and along the longitudinal axis of, the quartz tube. Catalyst to be tested, for MA-synthesis performance-determination purposes, was placed in the quartz tube and about the thermowell, forming an annular catalyst bed. Each bed of catalyst contained about 2 to about 3 grams of catalyst having a particle size of about 20 to about 40 mesh (U.S. Sieve). A spun quartz plug supported each catalyst bed.

The trioxane was thermally cracked by passing the feed through a hot reactor zone, heated to a temperature of about 390° C. (about 735° F.) to about 440° C. (about 825° F.), and located above the catalyst zone, prior to passing the feed through the catalyst bed.

The minireactor was operated at WHSV values between about 1.0 and about 3.2. Variations in the WHSV value within this range were not observed to affect the relationship between conversion and selectivity of the catalysts being tested.

The vapor-phase synthesis of methacrylic acid from propionic acid commonly produces coke, which is observed to deposit on the catalyst surface. Such coke deposits are usually removed from the catalyst by burning off with oxygen utilizing dilute air. Typically, catalyst decoking is effected whenever MA-synthesis performance of the catalyst falls below a predetermined criterion, such as a given value of percent conversion of PA to MA.

Initial performance studies were generally carried out by subjecting each investigated catalyst to appropriate MA-synthesis conditions for about 30 minutes prior to collecting the desired number of aliquot samples for analytical purposes, and thereafter decoking with air before removing additional aliquot samples. This particular catalyst decoking procedure was utilized to reduce the likelihood of a variable build-up of coke upon the catalyst, which might affect evaluation of catalyst performance.

General sampling procedures, for analytical purposes, included collection of about 10 to about 25 grams of the reactor effluent in a tared U-tube, or Erlenmeyer-type receiver containing about 10 to about 25 grams of isopropanol at room temperature (i.e. about 25° C.). Reactor effluent samples were thereafter analyzed via gas chromatography (GC), employing internal-standard techniques. That is, the GC response for each of the organic components in the minireactor effluent was based upon the known response of the GC to an internal standard added to the sample. Actual PA titrations indicated that the propionic acid used in the feed was about 99.6 to about 99.9% pure.

Unless otherwise stated, pore volume, surface area and average pore diameter were determined by the BET nitrogen desorption test.

Each of the Tables appearing below presents the MA-synthesis performance data of a single catalyst over a period of time, unless stated otherwise.

The stated percentages of $SiO_2$, $SnO_2$ and certain other materials were based upon the weight of the $SiO_2$-$SnO_2$ mixed-oxides. The stated percentages of cesium were based on the weight of the catalyst.

EXAMPLES

EXAMPLE 1

Catalyst Containing About 4 wt. % Cs+1 on 50-50 wt. % $SiO_2$-$SnO_2$ Mixed-Oxide Support A slurry was formed by combining, with agitation, particulate $SnO_2$ (about 50 grams) suspended in deionized water (about 125 milliliters), $Cs_2CO_3$ (about 5 grams) dissolved in water (about 10 milliliters) and silica sol (Nalco 1034-A silica sol). Ammonium nitrate (about 5 grams) in water (5 milliliters) was also added. The resulting admixture was left standing and was observed to gel in about 1 hour.

Thereafter, the obtained gel was dried in a microwave oven to constant weight, and then crushed. The dried-and-crushed gel was calcined at a temperature of about 540° C. (about 1000° F.) for about 8 hours. A catalyst containing about 4 wt. % Cs on a $SiO_2$-$SnO_2$ mixed-oxide of about 50-50 wt. % $SiO_2$/ $SnO_2$ was obtained.

A Cs+1-on-silica gel "control" catalyst was prepared in substantially the same manner, except that particulate $SnO_2$ was omitted and replaced by an equivalent amount of silica. In particular, the silica control catalyst was prepared by combining with agitation silica sol (about 280 grams of Nalco 1034-A silica sol), boric acid (about 0.3 grams in about 15 ml. of deionized water), and $Cs_2CO_3$ (about 5 grams in about 50 ml. of deionized water). After the combined ingredients had been stirred for about 15 minutes, $NH_4NO_3$ (about 2.8 grams) was added to the mixture. The pH of the mixture was adjusted to 7.0 by the addition of concentrated nitric acid ($HNO_3$). After gelation, the catalyst was dried to constant weight in a microwave oven, and calcined at 540° C. (about 1000° F.) for about 8 hours. A Cs+1-on-silica control catalyst having a Cs content of about 3.75 wt. %, based on the weight of the catalyst, was obtained. While the control catalyst make up composition included about 500 parts by weight of boron per million parts by weight of the catalyst (p.p.m.), the presence of this level of boron was not observed to affect the catalyst performance.

Each of the catalysts thus produced was then subjected to MA-synthesis performance testing in the laboratory minireactor. The MA-synthesis performance data of the control catalyst is presented in Table I, and that of the $SiO_2$/ $SnO_2$ mixed-oxide catalyst is presented in Table II, below.

The performance of the control catalyst (Table I) was determined in the laboratory minireactor at a temperature ranging from about 297° C. (about 567° F.) to about 350° C. (about 662° F.), and at a WHSV value ranging from about 1.03 to about 2.60 hr.−1

TABLE I

MA-Synthesis Performance of a 3.75 wt. % Cs on Silica Catalyst

| Run No. | % PAC | % PAS | % PAY | T (°C.) | WHSV | % S A | % S B | % S 3-P |
|---|---|---|---|---|---|---|---|---|
| 1 | 48 | 65 | 31 | 350 | 1.45 | 9.1 | 4.7 | 1.1 |
| 2 | 41 | 76 | 31 | 333 | 1.46 | 4.7 | 2.6 | 0.7 |
| 3 | 38 | 79 | 30 | 327 | 1.46 | 4.4 | 2.3 | 0.8 |
| 4 | 35 | 82 | 29 | 320 | 1.46 | 3.4 | 1.8 | 0.7 |
| 5 | 31 | 89 | 27 | 315 | 1.46 | 3.1 | 1.6 | 0.8 |
| 6 | 27 | 94 | 25 | 308 | 1.46 | 2.6 | 1.4 | 0.4 |
| 7 | 25 | 93 | 23 | 304 | 1.47 | 2.1 | 1.1 | 0.8 |
| 8 | 28 | 93 | 26 | 312 | 1.46 | 2.6 | 1.4 | 0.8 |
| 9 | 26 | 93 | 24 | 307 | 1.46 | 2.3 | 1.2 | 0.6 |
| 10 | 32 | 88 | 28 | 318 | 1.47 | 3.1 | 1.6 | 0.6 |
| 11 | 31 | 84 | 26 | 314 | 1.47 | 2.5 | 1.4 | 0.7 |
| 12 | 34 | 82 | 28 | 319 | 1.49 | 2.9 | 1.5 | 0.7 |
| 13 | 36 | 81 | 29 | 326 | 1.48 | 3.8 | 1.9 | 0.7 |
| 14 | 29 | 82 | 24 | 325 | 2.55 | 2.1 | 1.6 | 0.8 |
| 15 | 30 | 86 | 26 | 330 | 2.55 | 2.9 | 2.1 | 1.1 |
| 16 | 38 | 74 | 28 | 320 | 1.04 | 3.7 | 1.7 | 0.8 |
| 17 | 25 | 87 | 22 | 319 | 2.53 | 1.9 | 1.4 | 1.0 |
| 18 | 33 | 78 | 26 | 310 | 1.04 | 3.0 | 1.4 | 0.8 |
| 19 | 22 | 83 | 18 | 310 | 2.57 | 1.3 | 1.2 | 0.9 |
| 20 | 31 | 73 | 23 | 302 | 1.04 | 2.0 | 0.9 | 0.6 |
| 21 | 19 | 78 | 15 | 302 | 2.60 | 0.6 | 0.6 | 0.9 |
| 22 | 27 | 81 | 22 | 297 | 1.03 | 1.5 | 0.8 | 0.6 |
| 23 | 15 | 92 | 14 | 297 | 2.55 | 1.1 | 0.7 | 0.9 |
| 24 | 47 | 67 | 32 | 350 | 1.50 | 6.9 | 3.7 | 1.1 |
| 25 | 31 | 83 | 26 | 315 | 1.50 | 2.4 | 1.6 | 0.7 |
| 26 | 31 | 82 | 26 | 316 | 1.50 | 2.5 | 1.3 | 0.7 |
| 27 | 30 | 87 | 26 | 315 | 1.47 | 2.5 | 1.4 | 0.7 |
| 28 | 28 | 89 | 25 | 314 | 1.48 | 2.0 | 1.3 | 0.8 |

Summarizing, the data of Table I show that at a PA conversion of about 30%, the selectivity to MA was about 86 to about 87%. (Run Nos. 15 and 27.) In particular, a temperature ranging from about 315° C. (about 599° F.) to about 330° C. (about 626° F.) at a WHSV ranging from about 1.47 to about 2.55 hr.−1 resulted in a PA conversion of about 30%.

The MA-synthesis performance data of two separate $SiO_2$-$SnO_2$ mixed-oxide cesium-containing catalysts was combined and is respectively presented in Table II, below. That is, Run Nos. 1-6 of Table II represent the MA-synthesis performance of one 4 wt. % Cs, 50-50 wt. % $SiO_2$-$SnO_2$ catalyst over time, and Run Nos. 7-26 represent the MA-synthesis data of another such catalyst, both prepared in a manner similar to that of EXAMPLE 1. These MA-synthesis catalyst performance data were obtained by employng separate laboratory minireactors.

TABLE II

MA-Synthesis Performance of 4 wt. % Cs, 50~50 wt. % $SiO_2$—$SnO_2$ Catalysts

| Run No. | % PAC | % PAS | % PAY | T (°C.) | WHSV | % S A | % S B | % S 3-P |
|---|---|---|---|---|---|---|---|---|
| 1 | 48 | 56 | 27 | 353 | 1.46 | 2.3 | 2.4 | 1.5 |
| 2 | 44 | 56 | 25 | 329 | 1.44 | 1.4 | 1.4 | 1.2 |
| 3 | 36 | 85 | 28 | 306 | 1.45 | 0.7 | 0.7 | 0.9 |
| 4 | 27 | 89 | 24 | 282 | 1.45 | 0.2 | 0.2 | 0.6 |
| 5 | 17 | 91 | 15 | 259 | 1.45 | 0.0 | 0.0 | 0.6 |
| 6 | 14 | 77 | 11 | 247 | 1.45 | 0.0 | 0.0 | 0.5 |
| 7 | 36 | 80 | 29 | 314 | 1.44 | 1.1 | 1.3 | 0.8 |
| 8 | 27 | 96 | 26 | 290 | 1.51 | 0.4 | 0.5 | 0.6 |
| 9 | 34 | 92 | 31 | 304 | 1.45 | 0.7 | 0.9 | 0.7 |
| 10 | 40 | 84 | 33 | 315 | 1.41 | 1.0 | 1.3 | 0.8 |
| 11 | 34 | 89 | 31 | 303 | 1.36 | 0.7 | 0.8 | 0.8 |
| 12 | 37 | 82 | 30 | 303 | 1.27 | 0.7 | 0.8 | 0.7 |
| 13 | 32 | 86 | 28 | 294 | 1.29 | 0.3 | 0.5 | 0.7 |
| 14 | 26 | 93 | 24 | 294 | 1.83 | 0.3 | 0.4 | 0.5 |
| 15 | 22 | 96 | 21 | 294 | 2.39 | 0.0 | 0.3 | 0.6 |
| 16 | 33 | 88 | 29 | 320 | 2.38 | 0.9 | 1.1 | 0.9 |
| 17 | 32 | 89 | 28 | 326 | 3.02 | 0.8 | 1.0 | 1.0 |
| 18 | 35 | 82 | 29 | 330 | 2.78 | 0.7 | 1.0 | 1.1 |
| 19 | 33 | 85 | 28 | 333 | 3.19 | 0.6 | 1.0 | 1.0 |
| 20 | 34 | 81 | 28 | 337 | 3.19 | 0.7 | 1.0 | 1.1 |
| 21 | 36 | 78 | 28 | 342 | 3.18 | 0.8 | 1.2 | 1.3 |
| 22 | 39 | 80 | 31 | 341 | 2.16 | 1.0 | 1.2 | 1.1 |
| 23 | 41 | 75 | 31 | 329 | 1.57 | 0.9 | 1.1 | 0.9 |
| 24 | 34 | 87 | 30 | 314 | 1.57 | 0.6 | 0.7 | 0.9 |
| 25 | 25 | 93 | 23 | 290 | 1.56 | 0.0 | 0.2 | 0.7 |
| 26* | 32 | 83 | 27 | 302 | 1.56 | 0.5 | 0.4 | 0.6 |

Summarizing, the data of Table II show that at about 30% conversion of PA, the selectivity to MA is at least about 89%. This value was determined employing a least-squares fit of the data.

The relatively lower temperature demonstrates that the $SiO_2$-$SnO_2$ mixed-oxide catalyst is more active than the silica control catalyst at about the same $Cs^{+1}$ level.

The relative selectivity toward the production of by-product A, for each of the $SiO_2$-$SnO_2$ mixed-oxide catalysts (Table II), and for the silica control catalyst (Table I), is shown in FIG. 1 as a functinn of PA conversion. Briefly, the $SiO_2$-$SnO_2$ mixed-oxide catalyst exhibits a reduced selectivity toward production of by-product A, as compared to the control catalyst, with each catalyst containing about 4 wt. % Cs based on the weight of the catalyst. In particular, at 30% conversion of PA to MA, the selectivity toward production of by-product A is about 0.4% when using the $SiO_2$-$SnO_2$ mixed-oxide catalyst of the present invention, as compared to about 2.7% using the control catalyst.

The data of Table II also show that the selectivity toward generation of by-product B is significantly less when using the $SiO_2$-$SnO_2$ mixed-oxide catalyst, as compared to the control catalyst. At 30% conversion of PA, for example, by-product B selectivity was about 0.7% for the $SiO_2$-$SnO_2$ mixed-oxide catalyst, as compared to about 2.2% using the control catalyst.

The overall comparative-performance data show that the 50-50 wt. % $SiO_2$-$SnO_2$ mixed-oxide supported catalyst is a relatively more active MA-synthesis catalyst than a comparable $SiO_2$ supported catalyst, as demonstrated by the relatively lower temperature needed for similar conversion. Also, the $SiO_2$-$SnO_2$ mixed-oxide supported catalyst exhibited a relatively higher selectivity toward production of MA, relative to production of the undesired by-products A, B and 3-P, than the comparable $SiO_2$ support catalyst. In particular, the amount of by-product A that was produced using the $SiO_2$-$SnO_2$ mixed-oxide catalyst of the present invention, for a given amount of MA, was less than that produced using the control, by a factor of about 6.

EXAMPLE 2

10 wt. % Cs on 50-50 wt. % $SiO_2$-$SnO_2$ and on 70-30 wt. % $SiO_2$-$SnO_2$ Catalysts $SiO_2$-$SnO_2$ mixed-oxide catalysts having relatively high cesium loadings (e.g. about 10 wt. % Cs) were prepared in a manner similar to EXAMPLE 1 and were found to possess excellent conversion and selectivity MA-synthesis performance characteristics. The 50-50 wt. % $SiO_2$-$SnO_2$ mixed-oxide catalyst was prepared utilizing $Cs_2CO_3$ and Nalco 2326 silica sol. The 70-30 wt. % $SiO_2$-$SnO_2$ mixed-oxide catalyst was prepared utilizing Nalco 1034-A silica sol.

Specifically, the 50-50 wt. % $SiO_2$-$SnO_2$ catalyst and the 70-30 wt. % $SiO_2$-$SnO_2$ catalyst, each at a 10 wt. % Cs loading, demonstrated a selectivity to by-product A, at 30% conversion of PA to MA, of less than about 0.1%. The observed data are presented in FIG. 1. While the observed reduced selectivity toward production of by-product A is somewhat lower than for the about 4 wt. % Cs-loaded $SiO_2$-$SnO_2$ catalyst discussed above in connection with EXAMPLE 1, it is markedly better (by a factor of about 25) than the selectivity of the about 4 wt. % Cs silica control catalyst of EXAMPLE 1.

The individual performance characteristics of these 50-50 wt. % $SiO_2$-$SnO_2$ and 70-30 wt. % $SiO_2$-$SnO_2$, 10 wt. % Cs, catalysts are presented in Tables III and IV, below. Specifically, Table III presents the 10 wt. % Cs, 50-50 wt. % $SiO_2$-$SnO_2$ MA-synthesis catalyst performance data, and Table IV presents the 10 wt. % Cs, 70-30 wt. % $SiO_2$-$SnO_2$ MA-synthesis catalyst performance data.

TABLE III

| | 10 wt. % Cs on 50~50 wt. % $SiO_2$—$SnO_2$ | | | | | | |
|---|---|---|---|---|---|---|---|
| Run No. | % PAC | % PAS | % PAY | T (°C.) | WHSV | % S A | % S B | % S 3-P |
| 1 | 26 | 86 | 22 | 298 | 1.55 | 0.2 | 0.5 | 0.4 |
| 2 | 34 | 83 | 28 | 307 | 1.54 | 0.2 | 0.8 | 0.4 |
| 3 | 38 | 80 | 31 | 317 | 1.54 | 0.4 | 1.2 | 0.6 |
| 4 | 45 | 68 | 31 | 327 | 1.55 | 0.5 | 1.5 | 0.6 |
| 5 | 28 | 92 | 26 | 292 | 1.54 | 0.0 | 0.5 | 0.5 |
| 6 | 32 | 88 | 28 | 304 | 1.55 | 0.2 | 0.6 | 0.5 |
| 7 | 32 | 89 | 28 | 306 | 1.63 | 0.6 | 0.7 | 0.6 |
| 8 | 28 | 86 | 24 | 305 | 2.48 | 0.0 | 0.5 | 0.4 |
| 9 | 32 | 82 | 26 | 316 | 2.46 | 0.0 | 0.7 | 0.6 |
| 10 | 28 | 90 | 25 | 298 | 1.55 | 0.0 | 0.5 | 0.4 |
| 11 | 28 | 90 | 25 | 297 | 1.56 | 0.0 | 0.5 | 0.4 |
| 12 | 33 | 84 | 28 | 307 | 1.55 | 0.2 | 0.7 | 0.4 |
| 13 | 35 | 86 | 30 | 316 | 1.55 | 0.3 | 1.0 | 0.7 |
| 14 | 41 | 76 | 32 | 327 | 1.53 | 0.5 | 1.4 | 0.7 |
| 15 | 26 | 94 | 24 | 292 | 1.52 | 0.0 | 0.4 | 0.6 |
| 16 | 32 | 89 | 29 | 303 | 1.28 | 0.2 | 0.8 | 0.6 |
| 17 | 31 | 90 | 28 | 304 | 1.50 | 0.2 | 0.7 | 0.6 |
| 18 | 32 | 90 | 29 | 308 | 1.54 | 0.2 | 0.8 | 0.6 |

TABLE IV

| | 10 wt. % Cs on 70-30 wt. % $SiO_2$—$SnO_2$ | | | | | | |
|---|---|---|---|---|---|---|---|
| Run No. | % PAC | % PAS | % PAY | T (°C.) | WHSV | % S A | % S B | % S 3-P |
| 1 | 21 | 85 | 18 | 296 | 1.62 | 0.0 | 0.8 | 0.4 |
| 2 | 28 | 89 | 25 | 305 | 1.60 | 0.0 | 0.6 | 0.6 |
| 3 | 32 | 88 | 28 | 310 | 1.58 | 0.2 | 0.7 | 0.6 |
| 4 | 39 | 77 | 30 | 320 | 1.47 | 0.3 | 1.0 | 0.6 |
| 5 | 40 | 77 | 31 | 326 | 1.54 | 0.4 | 1.3 | 0.8 |
| 6 | 35 | 80 | 28 | 326 | 2.39 | 0.2 | 0.8 | 0.8 |
| 7 | 35 | 83 | 29 | 332 | 2.37 | 0.3 | 1.1 | 0.9 |
| 8 | 32 | 88 | 28 | 306 | 1.42 | 0.0 | 0.6 | 0.7 |
| 9 | 34 | 87 | 30 | 315 | 1.43 | 0.2 | 0.8 | 0.8 |
| 10 | 27 | 94 | 25 | 298 | 1.33 | 0.0 | 0.4 | 0.6 |
| 11 | 30 | 91 | 28 | 306 | 1.33 | 0.3 | 0.6 | 0.6 |
| 12 | 30 | 90 | 27 | 311 | 1.64 | 0.0 | 0.6 | 0.7 |
| 13 | 36 | 80 | 29 | 320 | 1.64 | 0.2 | 0.8 | 0.6 |
| 14 | 37 | 84 | 31 | 327 | 1.63 | 0.3 | 1.0 | 0.8 |
| 15 | 30 | 87 | 26 | 326 | 2.72 | 0.0 | 0.6 | 0.8 |
| 16 | 30 | 90 | 27 | 306 | 1.60 | 0.0 | 0.5 | 0.6 |

Briefly, each of these catalysts is seen to exhibit an average selectivity toward production of MA, at about 30% conversion of PA, of about 89%.

EXAMPLE 3

Effect of Varying the Relative Amounts of $SiO_2$-to-$SnO_2$, at about 7 wt. % Cs A series of catalysts containing about 7 wt. % Cs, and varying relative amounts of $SiO_2$-to-$SnO_2$, were investigated. Catalysts containing $SnO_2$ at levels of about 30%, about 40%, about 50%, about 60%, and about 70%, were each prepared using Nalco 2326 silica sol in a manner similar to EXAMPLE 1. The MA-synthesis performance data of these catalysts are presented below in Tables V-IX, below. The 7 wt. % Cs, 40-60 wt. % $SiO_2$-$SnO_2$ catalyst MA-synthesis performance data is presented in Table V, and the data of the 30-70 wt. % $SiO_2$-$SnO_2$ catalyst is presented in Table VI. The 7 wt. % Cs, 70-30 wt. % $SiO_2$-$SnO_2$ catalyst MA-synthesis performance data is presented in Table VII, while the data of the 60-40 wt. % $SiO_2$-$SnO_2$ catalyst is presented in Table VIII. The 7 wt. % Cs, 50-50 wt. % $SiO_2$-$SnO_2$ catalyst MA-synthesis performance data is presented in Table IX.

TABLE V 7 wt. % Cs, 40–60 wt. % SiO₂—SnO₂

| Run No. | % PAC | % PAS | % PAY | T (°C.) | WHSV | % S A | % S B | % S 3-P |
|---|---|---|---|---|---|---|---|---|
| 1 | 28.3 | 91 | 26 | 284 | 1.46 | 0.5 | 0.6 | 1.5 |
| 2 | 37.8 | 87 | 33 | 294 | 1.43 | 0.7 | 0.8 | 1.0 |
| 3 | 40.8 | 86 | 35 | 302 | 1.55 | 0.8 | 1.0 | 1.0 |
| 4 | 42.5 | 80 | 34 | 309 | 1.39 | 1.4 | 1.6 | 1.1 |
| 5 | 45.2 | 72 | 32 | 320 | 1.47 | 1.5 | 1.9 | 1.2 |
| 6 | 22.8 | 93 | 21 | 267 | 1.44 | 0.0 | 0.2 | 1.0 |
| 7 | 30.2 | 92 | 28 | 285 | 1.46 | 0.2 | 0.3 | 1.0 |
| 8 | 27.4 | 93 | 26 | 278 | 1.36 | 0.2 | 0.3 | 1.0 |
| 9 | 39.8 | 84 | 34 | 302 | 1.38 | 0.7 | 0.9 | 1.0 |

TABLE VI 7 wt. % Cs, 30–70 wt. % SiO₂—SnO₂

| Run No. | % PAC | % PAS | % PAY | T (°C.) | WHSV | % S A | % S B | % S 3-P |
|---|---|---|---|---|---|---|---|---|
| 1 | 22.0 | 85 | 19 | 283 | 1.52 | 0.3 | 0.3 | 0.8 |
| 2 | 30.3 | 89 | 27 | 293 | 1.46 | 0.0 | 0.4 | 0.7 |
| 3 | 35.8 | 85 | 31 | 306 | 1.45 | 0.2 | 0.8 | 0.7 |
| 4 | 40.2 | 80 | 32 | 317 | 1.38 | 0.3 | 1.2 | 1.0 |
| 5 | 43.5 | 72 | 31 | 328 | 1.50 | 0.5 | 1.8 | 1.1 |
| 6 | 20.6 | 93 | 19 | 268 | 1.47 | 0.0 | 0.4 | 0.7 |
| 7 | 34.3 | 83 | 28 | 300 | 1.46 | 0.0 | 0.5 | 0.7 |

TABLE VII 7 wt. % Cs, 70–30 wt. % SiO₂—SnO₂

| Run No. | % PAC | % PAS | % PAY | T (°C.) | WHSV | % S A | % S B | % S 3-P |
|---|---|---|---|---|---|---|---|---|
| 1 | 26.7 | 90 | 24 | 297 | 1.66 | 1.8 | 1.2 | 1.0 |
| 2 | 35.0 | 85 | 30 | 306 | 1.68 | 2.6 | 2.0 | 0.8 |
| 3 | 41.5 | 74 | 31 | 314 | 1.71 | 3.0 | 2.6 | 0.9 |
| 4 | 44.4 | 71 | 32 | 323 | 1.71 | 3.6 | 3.3 | 1.1 |
| 5 | 29.6 | 85 | 25 | 288 | 1.74 | 0.9 | 0.9 | 0.8 |
| 6 | 33.6 | 85 | 29 | 298 | 1.66 | 1.5 | 1.4 | 0.9 |
| 7 | 37.9 | 78 | 30 | 306 | 1.76 | 2.0 | 1.9 | 1.0 |
| 8 | 23.9 | 88 | 21 | 280 | 1.74 | 0.4 | 0.4 | 0.8 |
| 9 | 28.0 | 82 | 23 | 286 | 1.74 | 0.7 | 0.7 | 0.8 |
| 10 | 29.8 | 88 | 26 | 292 | 1.72 | 1.0 | 0.9 | 0.9 |
| 11 | 35.2 | 78 | 28 | 298 | 1.76 | 1.4 | 1.4 | 0.9 |

TABLE VIII 7 wt. % Cs, 60–40 wt. % SiO₂—SnO₂

| Run No. | % PAC | % PAS | % PAY | T (°C.) | WHSV | % S A | % S B | % S 3-P |
|---|---|---|---|---|---|---|---|---|
| 1 | 22.9 | 94 | 21 | 286 | 1.58 | 1.0 | 0.7 | 0.9 |
| 2 | 32.0 | 90 | 29 | 296 | 1.58 | 1.5 | 1.2 | 0.9 |
| 3 | 39.5 | 83 | 33 | 305 | 1.58 | 2.0 | 1.6 | 1.1 |
| 4 | 44.8 | 75 | 34 | 314 | 1.58 | 2.6 | 2.3 | 1.2 |
| 5 | 24.9 | 91 | 23 | 277 | 1.59 | 0.3 | 0.3 | 1.0 |
| 6 | 29.8 | 89 | 26 | 287 | 1.59 | 0.8 | 0.7 | 1.0 |
| 7 | 34.0 | 85 | 29 | 292 | 1.58 | 0.9 | 0.8 | 1.1 |
| 8 | 36.4 | 86 | 31 | 298 | 1.58 | 1.4 | 1.3 | 1.0 |

TABLE IX 7 wt. % Cs, 50–50 wt. % SiO₂—SnO₂

| Run No. | % PAC | % PAS | % PAY | T (°C.) | WHSV | % S A | % S B | % S 3-P |
|---|---|---|---|---|---|---|---|---|
| 1 | 22.7 | 85 | 19 | 282 | 1.56 | 0.4 | 0.5 | 0.9 |
| 2 | 32.5 | 90 | 29 | 293 | 1.56 | 0.7 | 0.8 | 0.8 |
| 3 | 39.4 | 85 | 34 | 303 | 1.56 | 1.0 | 1.1 | 0.8 |
| 4 | 43.7 | 80 | 35 | 312 | 1.56 | 1.1 | 1.3 | 0.9 |
| 5 | 32.7 | 77 | 25 | 282 | 1.55 | 0.2 | 0.2 | 0.7 |
| 6 | 33.6 | 89 | 30 | 290 | 1.58 | 0.4 | 0.5 | 0.8 |
| 7 | 37.3 | 89 | 33 | 299 | 1.50 | 0.6 | 0.9 | 0.9 |
| 8 | 40.3 | 86 | 35 | 304 | 1.43 | 0.9 | 1.1 | 0.8 |
| 9 | 22.7 | 94 | 21 | 271 | 1.57 | 0.0 | 0.3 | 0.5 |
| 10 | 25.4 | 93 | 24 | 278 | 1.58 | 0.0 | 0.3 | 0.7 |
| 11 | 26.5 | 94 | 25 | 282 | 1.58 | 0.3 | 0.3 | 0.9 |
| 12 | 32.9 | 90 | 30 | 292 | 1.56 | 0.4 | 0.5 | 0.9 |
| 13 | 37.4 | 87 | 33 | 300 | 1.48 | 0.6 | 0.9 | 0.9 |
| 14 | 48.3 | 72 | 34 | 318 | 1.41 | 1.3 | 1.6 | 1.0 |

Also presented below is Table X which summarizes the percent cesium present on the catalyst, the surface area (S.A.), and the cesium ion site density for a number of catalysts produced and tested in the manner set forth herein. In particular, the above-discussed catalysts of Tables V–IX, and the 10 wt. % Cs, 50–50 wt. % SiO₂-SnO₂ mixed-oxide catalyst discussed above in connection with Table III of EXAMPLE 2, as well as a catalyst presented in Table XV of EXAMPLE 5, below, are all compared at a conversion value of about 35% PAC.

TABLE X

Cesium Ion Site Densities

| Catalyst[a] of | % Cs Fresh/Ave.[b] | S.A. Fresh/Ave.[b] | Cs/nm² Fresh/Ave.[b] | Ave.[b] Sel. at 35% PAC |
|---|---|---|---|---|
| Table III | 9.4/8.5 | 63/58 | 6.8/6.6 | 84 |
| Table V | 6.7/6.5 | 136/108 | 2.2/2.9 | 91 |
| Table VI | 7.2/7.0 | 64/54 | 5.1/6.0 | 85 |
| Table VII | 6.8/6.6 | 210/170 | 1.5/1.9 | 81 |
| Table VIII | 6.6/6.5 | 171/137 | 1.8/2.3 | 86 |
| Table IX | 6.6/6.6 | 134/106 | 2.2/3.0 | 90 |
| Table XV[c] | 6.7/7.8 | 311/222 | 1.0/2.0 | 69 |

[a]All catalysts were prepared from Nalco 2326 silica sol.
[b]Average = ("fresh" or initial value + used value)/2.
[c]Presented in EXAMPLE 5, below.

For these various catalysts, briefly, a cesium ion site density of about 2.2 Cs/nm² (catalyst of Table V) appears to be optimal from the standpoint of selectivity at about 35% PAC, although a site density ranging from about 1.5 to at least about 6.8 cesium ions per square nanometer of the catalyst support surface area is also seen to result in the production of a MA-synthesis catalyst having markedly superior MA-synthesis performance characteristics.

Some of the 7 wt. % Cs catalyst performance data, i.e. that of Tables V and IX, were plotted and compared to the MA-synthesis performance data obtained from a 7 wt. % Cs catalyst containing no SnO₂. This comparison is shown in FIG. 2 from which it can be seen that the presence of SnO₂ in the present catalyst support noticeably enhances the MA-synthesis performance of the Cs-bearing catalyst support of the present invention, as distinguished from a control catalyst in which Cs is supported on silica only. Also, FIG. 2 generally illustrates the relationship between conversion and selectivity of the catalysts being tested.

EXAMPLE 4

Other Mixed-Oxide Supports

The inclusion of Bi₂O₃, GeO₂ and TiO₂ into a silica catalyst support was also investigated. It was found that Cs catalysts supported on SiO₂/Bi₂O₃ and SiO₂/TiO₂ performed generally poorly as MA-synthesis catalysts. Cs catalysts supported on SiO₂/GeO₂ exhibited an unacceptably short life under process conditions investigated. The observed performance data are presented in Tables XI–XIV, below. The MA-synthesis performance data of the catalyst containing $Bi_2O_3$ is presented in Table XI, while the data of the catalyst containing $TiO_2$ is presented in Table XIV. The MA-synthesis performance data of the catalyst containing $GeO_2$ is presented in Tables XII and XIII.

Except as noted below, these catalysts were made in substantially the same manner as the $SiO_2/SnO_2$ mixed-oxide supported catalyst of EXAMPLE 1. The 10 wt. % Cs, $SiO_2$-$Bi_2O_3$ catalyst (Table XI) was made using Nalco 1034-A silica sol. Each of the 7 wt. % Cs, $SiO_2$-$GeO_2$ catalysts (Tables XII and XIII) was made using Nalco 2326 silica sol. One of the $SiO_2$-$GeO_2$ catalysts (Table XII) was calcined at about 350° C. (about 660° F.); the other (Table XIII) was calcined at about 540° C. (about 1000° F.). The 4 wt. % Cs, $SiO_2$-$TiO_2$ catalyst (Table XIV) was made using Nalco 1034-A silica sol.

TABLE XI 10 wt. % Cs, 50—50 wt. % $SiO_2$—$Bi_2O_3$

| Run No. | % PAC | % PAS | % PAY | T (°C.) | WHSV | % S A | % S B | % S 3-P |
|---|---|---|---|---|---|---|---|---|
| 1 | 14 | 88 | 12 | 289 | 1.48 | 0.0 | 0.6 | 0.7 |
| 2 | 15 | 79 | 12 | 298 | 1.50 | 0.0 | 0.6 | 0.5 |
| 3 | 18 | 88 | 15 | 308 | 1.45 | 0.0 | 1.0 | 0.8 |
| 4 | 22 | 76 | 17 | 319 | 1.42 | 0.2 | 1.3 | 0.8 |
| 5 | 25 | 73 | 18 | 325 | 1.45 | 0.3 | 1.5 | 0.9 |
| 6 | 30 | 63 | 19 | 332 | 1.52 | 0.4 | 1.6 | 0.7 |

TABLE XII 7 wt. % Cs, 50—50 wt. % $SiO_2$—$GeO_2$, Calcined at 350° C.

| Run No. | % PAC | % PAS | % PAY | T (°C.) | WHSV | % S A | % S B | % S 3-P |
|---|---|---|---|---|---|---|---|---|
| 1 | 39.2 | 86 | 34 | 310 | 1.42 | 0.5 | 0.7 | 1.2 |
| 2 | 33.9 | 82 | 28 | 320 | 1.44 | 0.2 | 0.6 | 0.8 |
| 3 | 29.0 | 80 | 23 | 334 | 1.46 | 0.3 | 1.1 | 0.8 |
| 4 | 31.8 | 81 | 26 | 340 | 1.37 | 0.4 | 1.1 | 1.2 |
| 5 | 21.6 | 88 | 19 | 298 | 1.43 | 0.0 | 0.2 | 0.9 |
| 6 | 25.3 | 84 | 21 | 309 | 1.39 | 0.0 | 0.3 | 0.9 |

TABLE XIII 7 wt. % Cs, 50—50 wt. % $SiO_2$—$GeO_2$, Calcined at 540° C.

| Run No. | % PAC | % PAS | % PAY | T (°C.) | WHSV | % S A | % S B | % S 3-P |
|---|---|---|---|---|---|---|---|---|
| 1 | 34.7 | 82 | 29 | 300 | 1.47 | 0.4 | 0.5 | 1.5 |
| 2 | 31.8 | 94 | 30 | 312 | 1.51 | 0.2 | 0.4 | 1.4 |
| 3 | 31.2 | 88 | 28 | 327 | 1.44 | 0.2 | 0.7 | 1.4 |
| 4 | 30.3 | 85 | 26 | 342 | 1.42 | 0.3 | 1.1 | 1.5 |
| 5 | 20.4 | 100 | 20 | 293 | 1.47 | 0.0 | 0.5 | 1.3 |

TABLE XIV 4 wt. % Cs, 50—50 wt. % $SiO_2$—$TiO_2$

| Run No. | % PAC | % PAS | % PAY | T (°C.) | WHSV | % S A | % S B | % S 3-P |
|---|---|---|---|---|---|---|---|---|
| 1 | 29.5 | 43 | 13 | 305 | 1.54 | 2.7 | 3.5 | 5.2 |
| 2 | 30.0 | 47 | 14 | 313 | 1.53 | 3.6 | 4.2 | 4.6 |
| 3 | 32.8 | 46 | 15 | 322 | 1.53 | 4.1 | 5.3 | 4.6 |
| 4 | 24.0 | 52 | 12 | 303 | 1.52 | 2.7 | 2.4 | 4.3 |

The 10 wt. % Cs, $Bi_2O_3$-containing mixed-oxide catalyst exhibited generally poor selectivity to MA, over a PA conversion range of about 14 to about 30%, as is shown by the performance data of Table XI. The overall MA-synthesis performance, considering either % PAC or % PAY, in particular, is noticeably poor. The 4 wt. % Cs, $TiO_2$-containing mixed-oxide catalyst likewise exhibited a generally poor selectivity to MA (Table XIV).

While preliminary screening of the catalysts containing about 7 wt. % Cs on a 50-50 wt. % $SiO_2$-$GeO_2$ mixed-oxide catalyst appear to indicate relatively favorable initial-performance characteristics (Tables XII and XIII), a rapid decrease in activity over the first day-on-feed was observed when employing these particular catalysts to synthesize MA from PA. One of the $GeO_2$-containing catalyst supports was calcined at about 350° C. (Table XII), whereas the other was calcined at about 540° C. (Table XIII) as mentioned above, with no noticeable difference in catalyst performance. In light of the rapid decrease in catalyst activity over time, other $GeO_2$-containing catalysts were not investigated further.

A catalyst, having a catalyst support that consisted essentially of equal amounts by weight of $SiO_2$-$SnO_2$, but contained no Cs, was also investigated. The MA-synthesis performance of this catalyst was found to be very poor.

EXAMPLE 5

7 wt. % Cs, 40-60wt. % $SiO_2$-$SnO_2$ Catalyst Having Relatively Small Average Pore Diameter Also investigated, under MA-synthesis conditions utilizing the minireactor, was a catalyst comprising about 7 wt. % cesium, based on the weight of the catalyst, and about 40-60 wt. % $SiO_2$-$SnO_2$, based on the weight of the $SiO_2$-$SnO_2$ mixed-oxide. This catalyst had a "fresh" or initial average pore diameter of about 36 Angstroms and a relatively high "fresh" or initial surface area of about 311 m$^2$/gram. The catalyst was prepared utilizing $Cs_2CO_2$, Nalco 2326 silica sol, and Nalco $SnO_2$ sol (TX-2146; about 21 wt. % $SnO_2$; and containing $SnO_2$ particles having an average particle diameter of about 40 Angstroms), in a manner similar to that of EXAMPLE 1. The MA-synthesis performance data from that investigation are presented in Table XV, below.

Summarizing, this catalyst generally exhibited poorer performance than the above-discussed comparable 7 wt. % Cs, 40-60 wt. % $SiO_2$-$SnO_2$ catalyst (Table V), which was found to have a relatively greater "fresh" or initial average pore diameter, i.e. about 94 Angstroms, and a relatively lower "fresh" or initial surface area, i.e. about 136 m$^2$/gram (see Table X, above).

This particular example underscores the desirability of having an initial average pore diameter of at least about 50 Angstroms, and an initial surface area of less than about 300 m$^2$/gram.

TABLE XV 7 wt. % Cs, 40-60 wt. % $SiO_2$—$SnO_2$ Catalyst, Small Average Pore Diameter

| Run No. | % PAC | % PAS | % PAY | T (°C.) | WHSV | % S A | % S B | % S 3-P |
|---|---|---|---|---|---|---|---|---|
| 1 | 20.9 | 68 | 14 | 293 | 1.58 | 1.4 | 0.7 | 2.8 |
| 2 | 21.7 | 66 | 14 | 303 | 1.57 | 1.6 | 0.8 | 2.7 |
| 3 | 16.4 | 86 | 14 | 314 | 1.58 | 0.3 | 1.1 | 4.8 |
| 4 | 28.8 | 59 | 17 | 326 | 1.58 | 2.4 | 1.6 | 2.3 |
| 5 | 31.7 | 59 | 19 | 338 | 1.58 | 3.1 | 2.2 | 2.0 |
| 6 | 35.3 | 56 | 20 | 349 | 1.59 | 3.5 | 2.7 | 1.9 |
| 7 | 25.0 | 82 | 20 | 293 | 1.57 | 0.7 | 0.5 | 1.0 |
| 8 | 30.0 | 78 | 24 | 304 | 1.58 | 1.2 | 1.0 | 1.2 |
| 9 | 33.3 | 72 | 24 | 317 | 1.58 | 1.7 | 1.4 | 1.2 |
| 10 | 37.0 | 65 | 24 | 328 | 1.58 | 2.0 | 1.7 | 1.1 |
| 11 | 39.0 | 60 | 23 | 340 | 1.58 | 2.4 | 2.1 | 1.2 |
| 12 | 40.3 | 60 | 24 | 346 | 1.58 | 3.3 | 2.8 | 1.4 |
| 13 | 33.6 | 74 | 25 | 303 | 1.59 | 1.0 | 0.9 | 0.9 |

TABLE XV-continued 7 wt. % Cs, 40-60 wt. % SiO$_2$—SnO$_2$
Catalyst, Small Average Pore Diameter

| Run No. | % PAC | % PAS | % PAY | T (°C.) | WHSV | % S A | % S B | % S 3-P |
|---|---|---|---|---|---|---|---|---|
| 14 | 25.2 | 71 | 18 | 288 | 1.59 | 0.7 | 0.5 | 0.8 |
| 15 | 29.2 | 76 | 22 | 293 | 1.58 | 0.7 | 0.5 | 0.8 |
| 16 | 31.7 | 80 | 25 | 306 | 1.58 | 1.0 | 0.8 | 0.8 |

EXAMPLE 6

5 wt. % Cs, 49-51 wt. % SiO$_2$-SnO$_2$ Catalyst Having Separate Cs/SiO$_2$ and SnO$_2$ Granules A two-component catalyst was prepared by mixing Cs/SiO$_2$ granules with SnO$_2$ granules. The Cs/SiO$_2$ component was prepared by combining Cs$_2$CO$_3$ (31.3 g, dissolved in 62 g of water) with Nalco 2326 silica sol (1379 g). After mixing thoroughly, three fourths of the solution was set aside. The remaining solution (368.2 g) was gelled by addition of 3.44 g of ammonium nitrate in a few ml of water. The gel was dried in a microwave oven to substantially constant weight, crushed, and calcined at 538° C. for 8 hours. The resulting material was found by atomic absorption spectroscopy to contain 9.7% Cs by weight and had a BET surface area of 157 m$^2$/g. It was ground to a 18/40 mesh material.

The SnO$_2$ component was prepared by mixing commercial SnO$_2$ powder (40 g) with water (30 g) to form a homogeneous paste. The paste was dried in a microwave oven to a mass of 48.5 g, crushed, and calcined at 538° C. for 8 hours. The resulting material has a BET surface area of 5 m$^2$/g. It was ground to 18/40 mesh.

For evaluation, 1.03 g of the Cs/SiO$_2$ material and 0.97 g of the SnO$_2$ material were placed in the microreactor described above such that the particles were distributed evenly. The composition of the total catalyst load was 5.00% Cs with the remainder being 49:51 SiO$_2$:SnO$_2$ by weight. The MA-synthesis performance of the catalyst was determined at temperatures between 269° C. and 348° C. at a WHSV value of 1.51. The performance data is presented in Table XVI below.

Runs 1-9 in Table XVI show performance which is similar to that of catalysts of similar overall composition set out in Example 3. Runs 10-13 in Table XVI show inferior performance to those of Example 3, however, indicating that the useful lifetime of this catalyst may be shorter.

TABLE XVI 5 wt. % Cs, 49-51 wt. % SiO$_2$—SnO$_2$
Catalyst Having Separate Cs/SiO$_2$ and SnO$_2$ Granules

| Run No. | % PAC | % PAS | % PAY | T (°C.) | WHSV | % S A | % S B | % S 3 P |
|---|---|---|---|---|---|---|---|---|
| 1 | 37.2 | 92 | 34 | 311 | 1.52 | 1.7 | 1.5 | 1.1 |
| 2 | 39.4 | 91 | 36 | 310 | 1.51 | 1.5 | 1.5 | 1.0 |
| 3 | 48.8 | 66 | 32 | 348 | 1.51 | 3.4 |  | 1.4 |
| 4 | 38.3 | 91 | 35 | 310 | 1.51 | 0.9 | 1.0 | 1.0 |
| 5 | 20.8 | 91 | 19 | 269 | 1.51 | 0.0 | 0.0 | 1.8 |
| 6 | 47.1 | 73 | 34 | 340 | 1.51 | 2.8 |  | 1.6 |
| 7 | 25.0 | 86 | 22 | 278 | 1.51 | 0.0 | 0.0 | 1.1 |
| 8 | 44.7 | 78 | 35 | 330 | 1.51 | 1.9 | 1.7 | 1.5 |
| 9 | 29.0 | 89 | 26 | 290 | 1.51 | 0.2 | 0.2 | 2.2 |
| 10 | 42.9 | 78 | 33 | 320 | 1.51 | 1.1 | 1.0 | 1.2 |
| 11 | 34.8 | 83 | 29 | 300 | 1.51 | 0.4 | 0.4 | 1.5 |
| 12 | 38.5 | 82 | 32 | 310 | 1.51 | 0.8 | 0.6 | 1.6 |
| 13 | 33.1 | 78 | 26 | 296 | 1.51 | 0.3 | 0.3 | 1.6 |

EXAMPLE 7

5 wt. % Cs, 49-51 wt. % SiO$_2$-SnO$_2$ Catalyst Having Cs/SiO$_2$ and SnO$_2$ as Separate Particles Within the Same Granule The two components, 9.7% by weight Cs/SiO$_2$ and the SnO$_2$ described in Example 6, were mixed together in a 1.03:0.97 weight ratio and ground finely with a mortar and pestle. The resulting powder was compacted into tablets in a hydraulic press at 12,000 pounds per square inch. The tablets were then crushed to 18/40 mesh. For evaluation, 2.00 g of the catalyst was placed in a microreactor and its performance was determined at temperatures between 270° C. and 340° C. at a WHSV value of 1.51. The performance data is presented in Table XVII below.

TABLE XVII 5 wt. % Cs, 49-51 wt. % SiO$_2$—SnO$_2$
Catalyst Having Cs/SiO$_2$ and SnO$_2$ as Separate
Particles Within the Same Granule

| Run No. | % PAC | % PAS | % PAY | T (°C.) | WHSV | % S A | % S B | % S 3 P |
|---|---|---|---|---|---|---|---|---|
| 1 | 29.4 | 86 | 25 | 300 | 1.52 | 1.2 | 0.9 | 1.2 |
| 2 | 34.2 | 86 | 29 | 300 | 1.52 | 1.2 | 1.2 | 1.0 |
| 3 | 49.0 | 66 | 32 | 340 | 1.51 | 3.9 | 1.7 | 1.3 |
| 4 | 22.0 | 88 | 19 | 270 | 1.51 | 0.0 | 0.0 | 1.3 |
| 5 | 47.1 | 73 | 35 | 330 | 1.49 | 2.7 | 1.6 | 1.1 |
| 6 | 25.5 | 91 | 23 | 280 | 1.52 | 0.2 | 0.2 | 1.4 |
| 7 | 42.8 | 83 | 35 | 320 | 1.51 | 1.7 | 1.6 | 1.0 |
| 8 | 37.3 | 86 | 32 | 305 | 1.53 | 0.8 | 0.8 | 0.8 |
| 9 | 38.1 | 87 | 33 | 310 | 1.52 | 1.1 | 1.0 | 0.9 |
| 10 | 35.2 | 85 | 30 | 300 | 1.51 | 0.6 | 0.6 | 1.2 |

A novel SiO$_2$-SnO$_2$ mixed-oxide, Cs-containing catalyst has been described hereinabove. Preferred methods for the production of such a catalyst and for its use also are described hereinabove. While the catalyst, its use and methods for making the catalyst have been described with reference to preferred embodiments, the present invention is not to be limited to these embodiments. On the contrary, alternative methods of making and using the catalyst will become apparent to those skilled in the art upon reading the foregoing description. For example, while the above-described methods set forth in detail for making the catalyst illustrate one aspect of the present invention, which results in the co-formation of the novel catalyst the SiO$_2$-SnO$_2$ mixed-oxide can be formed first, and thereafter, cesium ions in the +1 oxidation state deposited onto the SiO$_2$-SnO$_2$ mixed-oxide surface. To that end, the SiO$_2$-SnO$_2$ mixed-oxide of the present invention can be contacted with an effective amount of a cesium ion-containing compound so that cesium ions are not only deposited onto the catalyst support surface in the +1 oxidation state, but so that the cesium ions are present on the catalyst support in an amount ranging between about 1 to about 15 percent by weight, based on the weight of the catalyst, as well. In other methods of preparation porous silica gel can be treated with a cesium compound and then mixed physically with tin (IV) oxide or porous silica gel can be ground with tin (IV) oxide and then compacted and made into proper size catalyst particles for commercial use. Still other variations within the spirit and scope of the present invention are possible and will readily present themselves to one skilled in the art.

What is claimed is:

1. A particulate catalyst, suitable for production of an alpha, beta-ethylenically unsaturated monocarboxylic acid by condensation of a saturated monocarboxylic acid with formaldehyde, which catalyst comprises:
- a $SiO_2$-$SnO_2$ mixed-oxide, constituted by a porous silica gel and $SnO_2$, and cesium ions in the +1 oxidation state;
- said $SiO_2$-$SnO_2$ mixed-oxide containing $SiO_2$ in an amount of about 5 to about 85 percent by weight and $SnO_2$ in an amount of about 95 to about 15 percent by weight, having a surface area of about 10 to about 300 $m^2$/gram, a porosity of less than about 5 $cm^3$/gram, and a pore size distribution such that less than about 10 percent of the pores present in the catalyst have a pore diameter greater than about 750 Angstroms; and
- said cesium ions being present on the surface of the mixed-oxide in an amount of about 1 to about 15 percent by weight based on the weight of the catalyst.

2. The catalyst in accordance with claim 1 wherein a major portion of said $SiO_2$-$SnO_2$ mixed-oxide is constituted by $SnO_2$.

3. The catalyst in accordance with claim 1 wherein said $SiO_2$-$SnO_2$ mixed-oxide contains about 30 to about 70 percent by weight $SiO_2$ and about 70 to about 30 percent by weight $SnO_2$.

4. The catalyst in accordance with claim 1 wherein said $SiO_2$-$SnO_2$ mixed-oxide contains about 40 to about 60 percent by weight $SiO_2$ and about 60 to about 40 percent by weight $SnO_2$.

5. The catalyst in accordance with claim 1 wherein said $SiO_2$-$SnO_2$ mixed-oxide contains about 40 to about 50 percent by weight $SiO_2$ and about 60 to about 50 percent by weight $SnO_2$.

6. The catalyst in accordance with claim 1 wherein said $SiO_2$-$SnO_2$ mixed-oxide contains about 50 percent by weight of each of $SiO_2$ and $SnO_2$.

7. The catalyst in accordance with claim 1 wherein the surface area is about 50 to about 135 $m^2$/gram.

8. The catalyst in accordance with claim 1 wherein the porosity is less than about 1 $cm^3$/gram.

9. The catalyst in accordance with claim 1 wherein a major portion of the pores present in the catalyst have a pore diameter of about 50 to about 500 Angstroms.

10. The catalyst in accordance with claim 1 wherein the pore diameter is about 80 to about 300 Angstroms.

11. The catalyst in accordance with claim 1 wherein the catalyst has an average cesium ion site density thereon of about 1 to about 10 cesium ions per square nanometer of the catalyst surface area.

12. The catalyst in accordance with claim 1 wherein the average cesium ion site density is about 2 to about 7 cesium ions per square nanometer of the catalyst surface area.

13. The catalyst in accordance with claim 1 wherein the cesium ions are present in an amount of about 4 to about 10 percent by weight.

14. The catalyst in accordance with claim 1 wherein the cesium ions are present in an amount of about 7 to about 10 percent by weight.

15. The catalyst in accordance with claim 1 wherein the cesium ions are present in an amount of about 4 percent by weight.

16. The catalyst in accordance with claim 1 wherein the cesium ions are present in an amount of about 7 percent by weight.

17. The catalyst in accordance with claim 1 wherein the cesium ions are present in an amount of about 10 percent by weight.

18. The catalyst in accordance with claim 1 wherein the mixed-oxide contains about 50 percent by weight of each of $SiO_2$ and $SnO_2$, and cesium ions in an amount of about 4 to about 10 percent by weight of the catalyst.

19. A method for making a cesium-containing catalyst containing a $SiO_2$-$SnO_2$ mixed-oxide and suitable for vapor-phase condensation of a saturated monocarboxylic acid with formaldehyde to produce an alpha, beta-ethylenically unsaturated monocarboxylic acid, which method comprises the steps of combining, with agitation, a silica sol having a silica particle diameter of about 50 to about 200 Angstroms, a slurry of $SnO_2$ and a cesium compound able to provide cesium in the +1 oxidation state on the catalyst support, in relative amounts sufficient to produce a freely-flowing slurry having a $SiO_2$/$SnO_2$ weight ratio of about 0.05 to about 6 and a $Cs/(SiO_2+SnO_2+Cs)$ weight ratio of about 0.01 to about 0.15;
- solidifying the produced, freely-flowing slurry to a gel;
- drying the obtained gel to a crushable solid state; and
- calcining the dried gel for a time period sufficient to remove adsorbed moisture therefrom.

20. The method in accordance with claim 19 wherein the silica sol is aqueous and has a silica content of about 14 to about 34 weight percent.

21. The method in accordance with claim 19 wherein said cesium compound is a salt selected from the group consisting of cesium carbonate, cesium hydroxide, cesium phosphate, cesium fluoride and cesium nitrate.

22. The method in accordance with claim 19 wherein said cesium compound is cesium propionate.

23. The method in accordance with claim 19 wherein the produced, freely-flowing slurry includes a gelling promoter.

24. The method in accordance with claim 23 wherein the gelling promoter is ammonium nitrate.

25. The method in accordance with claim 19 wherein the pH of the produced, freely-flowing slurry is adjusted to a value of about 7 prior to solidification.

26. The method in accordance with claim 25 wherein the pH value is adjusted by adding to the freely-flowing slurry an inorganic acid.

27. The method in accordance with claim 26 wherein the inorganic acid is nitric acid.

28. The method in accordance with claim 19 wherein, prior to drying, the gel is formed into a desired configuration, and is then dried.

29. The method in accordance with claim 19 wherein the drying is carried out at about atmospheric pressure.

30. The method in accordance with claim 19 wherein the drying is carried out at a temperature below about 150° C. and at a subatmospheric pressure.

31. The method in accordance with claim 19 wherein the gel is dried to substantially constant weight.

32. The method in accordance with claim 19 wherein the dried gel is comminuted.

33. The method in accordance with claim 19 wherein the calcining of the dried gel is carried out for a time period sufficient to reduce the weight of the dried gel by at least about 2 weight percent.

34. The method in accordance with claim 19 wherein the calcining of the dried gel is carried out at a temperature of about 540° C. for a time period of about 8 hours.

35. A method for making a $SiO_2$-$SnO_2$ mixed-oxide which comprises the steps of
- combining, with agitation, respective effective amounts of a silica sol containing silica particles of about 50 to about 200 Angstroms in diameter, and a slurry of $SnO_2$ containing particles of $SnO_2$ to produce a freely-flowing slurry having a $SiO_2/SnO_2$ weight ratio of about 0.05 to about 6;

solidifying the produced, freely-flowing slurry to a gel;

drying the obtained gel to a crushable solid state; and calcining the dried gel for a time period sufficient to remove adsorbed moisture therefrom.

36. The method in accordance with claim 35 wherein the silica sol is aqueous and has a silica content of about 14 to about 34 weight percent.

37. The method in accordance with claim 34 wherein the produced, freely-flowing slurry includes a gelling promoter.

38. A particulate catalyst, suitable for production of an alpha, beta-ethylenically unsaturated monocarboxylic acid by condensation of a saturated monocarboxylic acid with formaldehyde, which catalyst comprises a catalyst support constituted by a porous silica gel, and $SnO_2$ having a particle size of no more than about 10 microns; and cesium ions in the $+1$ oxidation state on the catalyst support surface;

said catalyst support containing $SiO_2$ in an amount of about 5 to about 85 percent by weight of the support and $SnO_2$ in an amount of about 95 to about 15 percent by weight of the support, having a surface area of about 10 to about 300 $m^2$/gram, a porosity of less than about 5 $cm^3$/gram, and a pore size distribution such that less than about 10 percent of the pores present in the catalyst have a pore diameter greater than about 750 Angstroms; and said cesium ions being present on the catalyst support surface in an amount of about 1 to about 15 percent by weight based on the weight of the catalyst.

* * * * *